(12) United States Patent
Laty

(10) Patent No.: US 10,456,589 B2
(45) Date of Patent: Oct. 29, 2019

(54) SYSTEM AND METHOD FOR PROVIDING HEAD-RELATED MEDICAL AND MENTAL HEALTH CONDITIONS

(71) Applicant: Mark Laty, Miami, FL (US)

(72) Inventor: Mark Laty, Miami, FL (US)

(*) Notice: Subject to any disclaimer, the term of this patent is extended or adjusted under 35 U.S.C. 154(b) by 284 days.

(21) Appl. No.: 15/420,767

(22) Filed: Jan. 31, 2017

(65) Prior Publication Data

US 2018/0214708 A1 Aug. 2, 2018

(51) Int. Cl.
| | | |
|---|---|---|
| A61N 2/00 | (2006.01) | |
| G02C 11/00 | (2006.01) | |
| A61N 5/06 | (2006.01) | |
| G02C 5/14 | (2006.01) | |
| G02C 7/10 | (2006.01) | |
| G02C 11/04 | (2006.01) | |

(52) U.S. Cl.
CPC ............ *A61N 2/002* (2013.01); *A61N 2/006* (2013.01); *A61N 5/0618* (2013.01); *G02C 5/14* (2013.01); *G02C 11/04* (2013.01); *G02C 11/10* (2013.01); *A61N 2005/0648* (2013.01)

(58) Field of Classification Search
CPC ...... A61N 2/002; A61N 2/006; A61N 5/0618; A61N 2005/0648; G02C 5/14; G02C 11/04; G02C 11/10
USPC .................. 600/9–15, 26–28; 607/88–95
See application file for complete search history.

(56) References Cited

U.S. PATENT DOCUMENTS

| | | | | |
|---|---|---|---|---|
| 3,658,051 A * | 4/1972 | MacLean | ............... | A61N 2/008 324/263 |
| 4,938,582 A * | 7/1990 | Leslie | ...................... | A61H 5/00 351/158 |
| 5,175,571 A * | 12/1992 | Tanefsky | ............... | G02C 5/001 351/158 |
| 5,389,981 A * | 2/1995 | Riach, Jr. | ............... | G02C 11/00 351/158 |
| 5,823,938 A * | 10/1998 | Hernandez | .............. | A61F 9/007 600/15 |
| 5,963,294 A * | 10/1999 | Schiffer | ................ | A61M 21/00 351/45 |
| 6,155,966 A * | 12/2000 | Parker | ...................... | A61N 2/02 600/13 |
| 6,406,419 B1 * | 6/2002 | Farahmand | .............. | A61N 2/06 351/158 |
| 7,901,071 B1 * | 3/2011 | Kulas | ..................... | G02C 11/04 351/158 |
| 8,956,396 B1 * | 2/2015 | Friend | .................. | A61N 5/0622 607/88 |
| 2002/0080326 A1 * | 6/2002 | Schleger | .................. | A61N 2/06 351/121 |

(Continued)

*Primary Examiner* — Navin Natnithithadha
*Assistant Examiner* — Sunita Reddy
(74) *Attorney, Agent, or Firm* — The Concept Law Group, PA; Scott D. Smiley; Scott M. Garrett

(57) ABSTRACT

A system and method for treating head-related medical and mental health conditions embodied in eyewear is provided. The eyewear provides transcranial magnetic stimulation and light therapy through an electromagnetic generator system and light sources, respectively, disposed along the frame of the eyewear. The electromagnetic generator system provides at least one pulse-generating stimulation arm along a frame arm, wherein the stimulation arm is movable between a storage and an operative condition directing magnetic pulses toward the wearer's skull. The light sources may be disposed along an inner lateral edge of the portions of the frame retaining the optical lenses so that the light sources direct adjustably angled dichroic light toward the eyes of a wearer.

7 Claims, 3 Drawing Sheets

(56) References Cited

U.S. PATENT DOCUMENTS

| | | | | |
|---|---|---|---|---|
| 2002/0198577 A1* | 12/2002 | Jaillet | .................... | A61M 21/00 607/88 |
| 2004/0010178 A1* | 1/2004 | Buckner | ................. | A61F 7/007 600/9 |
| 2006/0069420 A1* | 3/2006 | Rademacher | ...... | A61N 1/36046 607/141 |
| 2008/0055537 A1* | 3/2008 | Asrani | .................... | H01Q 1/273 351/41 |
| 2008/0269849 A1* | 10/2008 | Lewis | ................. | A61N 5/0613 607/91 |
| 2009/0287035 A1* | 11/2009 | Dietrich | ............. | A61N 1/36017 600/9 |
| 2010/0036488 A1* | 2/2010 | de Juan, Jr. | ................ | A61F 2/14 623/5.16 |
| 2010/0179469 A1* | 7/2010 | Hammond | ........... | A61N 5/0603 604/20 |
| 2011/0282129 A1* | 11/2011 | Rigaux | ................ | A61N 1/0456 600/26 |
| 2011/0319958 A1* | 12/2011 | Simon | .................... | A61N 2/006 607/42 |
| 2012/0215291 A1* | 8/2012 | Pugh | ..................... | A61M 21/02 607/93 |
| 2012/0235900 A1* | 9/2012 | Border | ..................... | G02B 5/23 345/156 |
| 2013/0282095 A1* | 10/2013 | Mignolet | ............. | A61N 1/0456 607/139 |
| 2013/0304162 A1* | 11/2013 | Veres | .................... | A61N 5/0613 607/88 |
| 2015/0313496 A1* | 11/2015 | Connor | ................ | A61B 5/0476 600/301 |
| 2017/0333725 A1* | 11/2017 | Hotani | ..................... | A61N 2/02 |
| 2018/0133507 A1* | 5/2018 | Malchano | ............ | A61N 5/0622 |

\* cited by examiner

SYSTEM AND METHOD FOR PROVIDING HEAD-RELATED MEDICAL AND MENTAL HEALTH CONDITIONS

BACKGROUND OF THE INVENTION

The present invention relates to medical devices embodying methods for treating head-related medical and mental health conditions and, more particularly, to a system and method of treating head-related medical conditions, neurological conditions, and mental health disorders and illnesses embodied in eyewear.

Transcranial Magnetic Stimulation (TMS) is a FDA approved treatment method for migraine. TMS, however, is currently provided through huge machines a user needs to be hooked up to in an office or hospital setting. As a result, the treatment sessions are not practical nor affordable to say the least. Using light therapy for treating certain mental disorders such as depression is another FDA-approved treatment. Currently, though, such therapy is only provided by requiring a user to sit in front of a light projector for extended periods of time without moving relative to the light projector. Thereby, like current TMS treatments, light therapy is also impractical for an on-the-go society. Because of the impracticalities inherent in each technology, there is no current system, method or device that conveniently combines both technologies.

As can be seen, there is a need for a system and method of treating head-related medical conditions, neurological conditions, and mental health disorders and illnesses embodied in eyewear. Such eyewear combines both TMS treatment and light therapy technologies, making them not only affordable but very practical forms of treatment for such disorders as migraines, depression, anxiety, epilepsy, schizophrenia and bipolar.

SUMMARY OF THE INVENTION

In one aspect of the present invention, a system and method of treating head-related medical conditions, neurological conditions, and mental health disorders and illnesses are embodied in headwear, wherein the systemic headwear is adapted to be worn on a head of a human user; an electromagnetic generator system provided by the headwear; and a stimulation arm electrically connected to the electromagnetic generator system, wherein the stimulation arm is pivotally connected to one of two frame arms of the headwear so that the stimulation arm is movable between a storage condition and an operative condition extending upwardly of said frame arm.

In another aspect of the present invention, the systemic eyewear includes a frame defining two lens portion, wherein each lens portion engages a periphery of an optical lens; and two frame arms, each frame arm extending from a respective opposing end of the frame; an electromagnetic generator system provided by the eyewear; and a stimulation arm electrically connected to the electromagnetic generator system, wherein the stimulation arm is pivotally connected to one of the two frame arms to be movable between a storage condition and an operative condition extending upwardly of said frame arm.

In yet another aspect of the present invention, the systemic eyewear includes a frame defining two lens portion, wherein each lens portion engages a periphery of an optical lens, wherein each optical lens is a transitional optical lens; and two frame arms, each frame arm extending from a respective opposing end of the frame; an electromagnetic generator system provided by the eyewear; a stimulation arm electrically connected to the electromagnetic generator system, wherein the stimulation arm is pivotally connected to one of the two frame arms to be movable between a storage condition and an operative condition extending upwardly of said frame arm; a stimulation plate electrically connected to the electromagnetic generator system, wherein the stimulation plate is disposed between the two lens portions; a plurality of light sources disposed along a lateral edge of at least one of the two lens portion, wherein the plurality of light sources provides dichroic light directed generally parallel to the respective optical lens; and at least one switch electrically connected to the plurality of light sources and the electromagnetic generator system for selectively operating the dichroic light and a magnetic pulsing emitted therefrom, respectively.

These and other features, aspects and advantages of the present invention will become better understood with reference to the following drawings, description and claims.

DETAILED DESCRIPTION OF THE INVENTION

Figure 1:
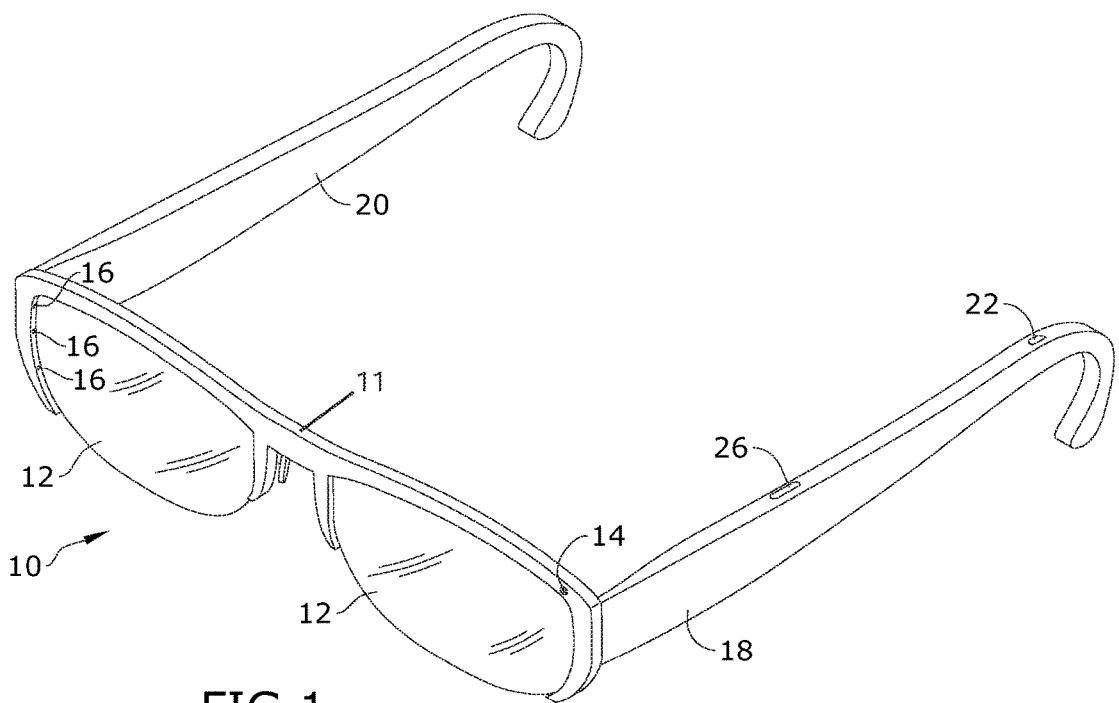
FIG. 1 is a front perspective of an exemplary embodiment of the present invention.
Figure 2:
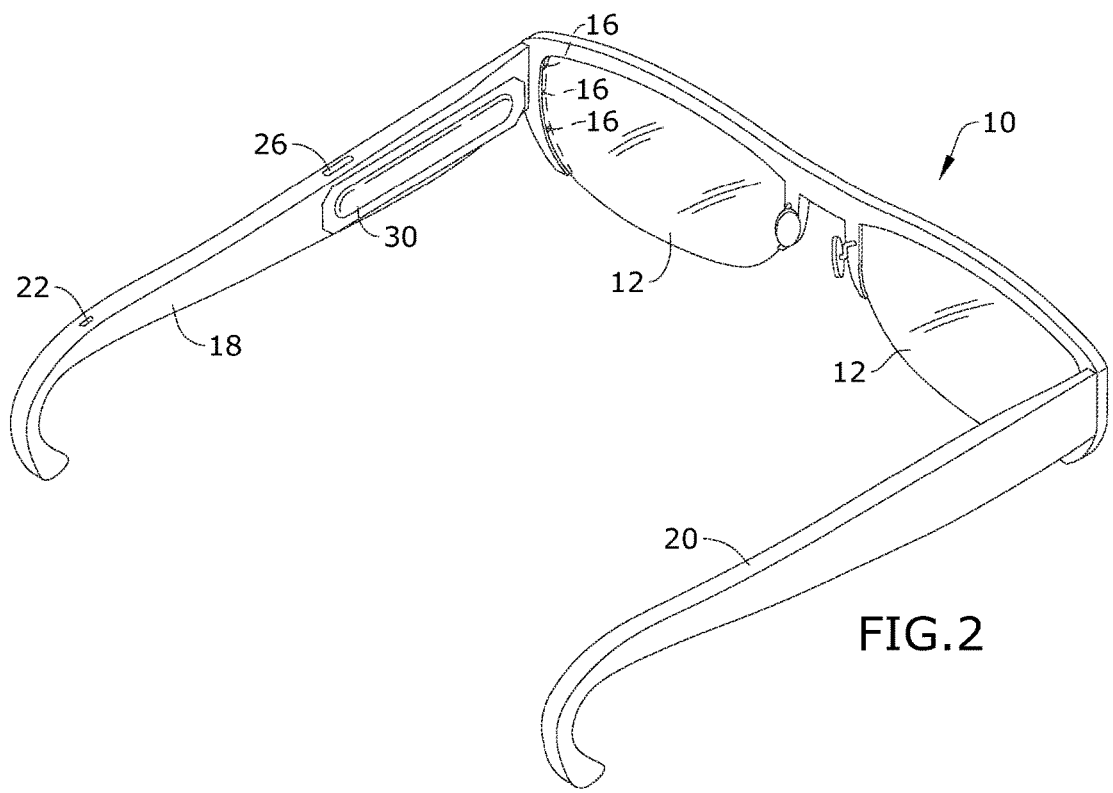
FIG. 2 is a rear perspective view of an exemplary embodiment of the present invention.
Figure 3:
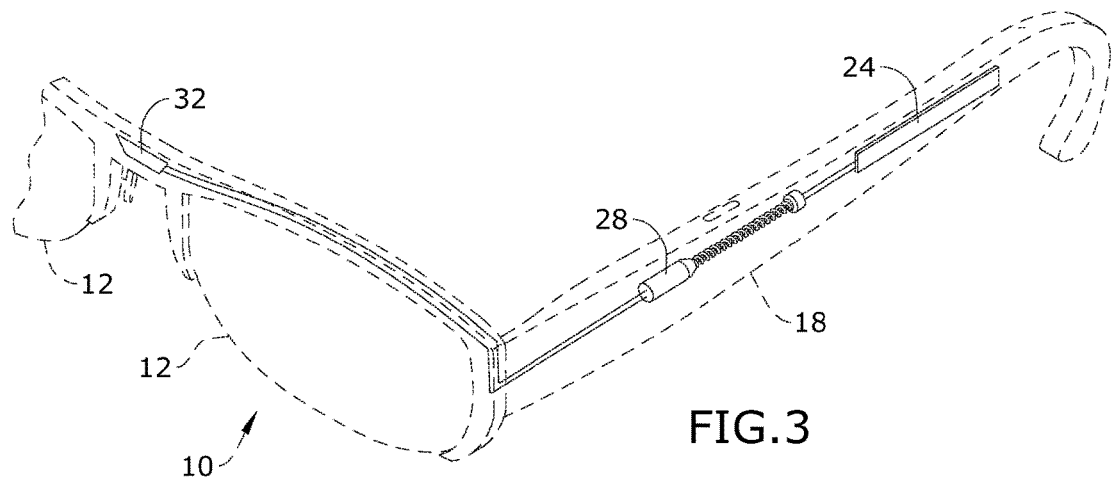
FIG. 3 is a detailed perspective of a electromagnetic generator system 28 of an exemplary embodiment of the present invention.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a system and method for treating head-related medical and mental health conditions embodied in eyewear. The eyewear provides transcranial magnetic stimulation and light therapy through an electromagnetic generator system and light sources, respectively, disposed along the frame of the eyewear. The electromagnetic generator system provides at least one pulse-generating stimulation arm along a frame arm, wherein the stimulation arm is movable between a storage and an operative condition directing magnetic pulses toward the wearer's skull. The light sources may be disposed along an inner lateral edge of the portions of the frame retaining the optical lenses so that the light sources direct adjustably angled dichroic light toward the eyes of a wearer.

Referring to FIGS. 1 through 5, the present invention may include an eyewear 10 dimensioned and adapted to be worn on the face of a human user. The eyewear 10 includes a frame 11 adapted to retain two optical lenses 12; two frame arms 18 and 20 extend from opposing ends of the frame 11. Generally, the frame 11 defines two cavities, each cavity engaging its respective optical lens 12 along its periphery. The optical lenses 12 may be transitional optical lenses, facilitating use of the eyewear in bright or dim lighting conditions. The frame arms 18 and 20 may be pivotally connected to their respective end of the frame 11.

Each frame arm 18 and 20 provides a temple surface facing the temple of the wearer.

Figure 4:
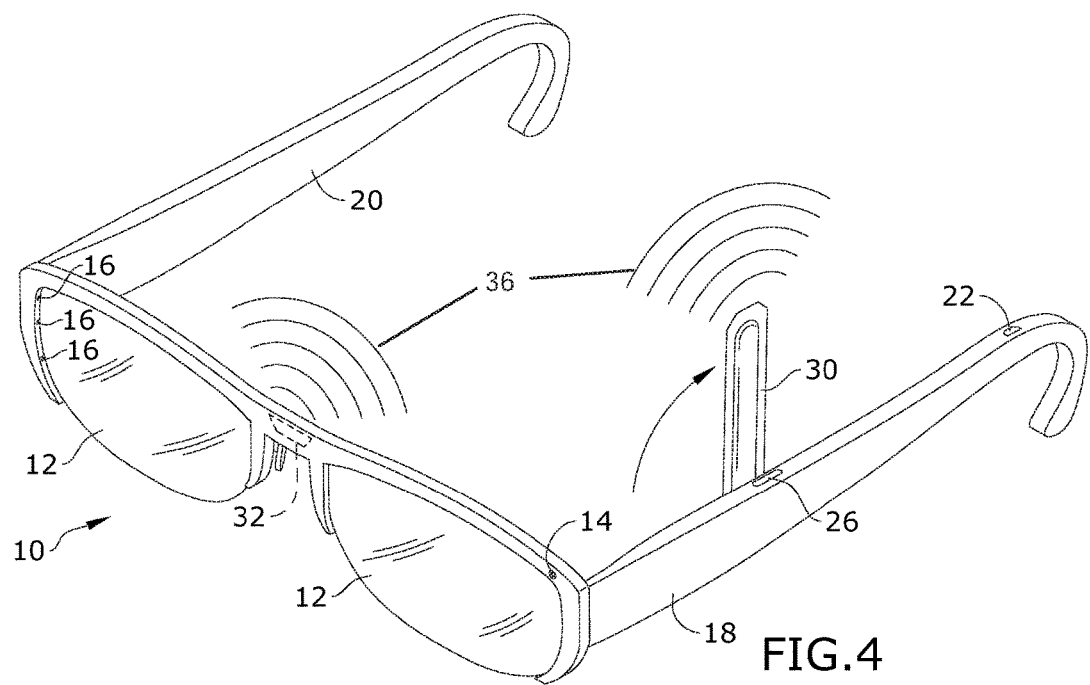
FIG. 4 is a perspective view of an exemplary embodiment of the present invention, showing the raising of a stimulation arm 30, and pulsing 36 of the stimulation arm 30 and stimulation plate 32.

The eyewear 10 may provide an electromagnetic generator system 28 adapted to produce magnetic pulsing 36 for transcranial magnetic stimulation (TMS). The electromagnetic generator system 28 may be electrically connected to a stimulation arm 30 and a stimulation plate 32, each of which act as a pulsing generator for emitting magnetic pulsing 36. The stimulation arm 30 may be pivotally connected to a temple surface of a frame arm so as to be movable between a storage condition and an operable condition, wherein, in the operable condition, the stimulation arm 30 is generally transverse to its respective frame arm 18 or 20 (or both) so as to extend upwardly adjacent to a temple of the wearer, as illustrated in FIG. 4.

The stimulation arm 30 may be provided along both frame arms 18 and 20, even though this is not specifically shown in the illustrations.

The stimulation plate 32 may be disposed near a midpoint of the frame 11, between the optical lenses 12 and thus between the eyes of the wearer so as to be directed to specific areas of the brain such as pre-frontal cortex, to a specific parietal area (for depression), and/or to other cerebral areas.

Figure 5:
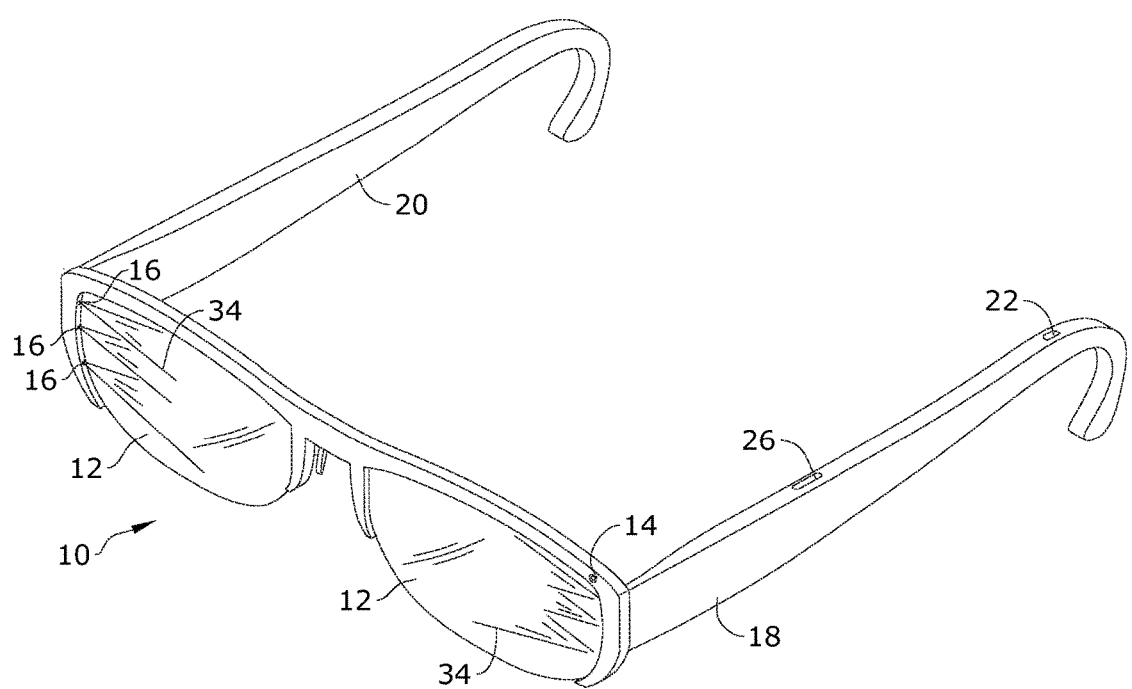
FIG. 5 is a perspective view of an exemplary embodiment of the present invention, showing the projection of a dichroic light 34 across the optical lenses 12.

Also, the eyewear 10 provides a plurality of light sources 16 disposed along an inner edge, or lateral side, of a portion of the frame 11 formed to retain the optical lenses 12, as illustrated in FIG. 5. The disposition of the light sources 16 may provide an adjustable angle or light path directed towards the eyes of the wearer. The light sources 16 may be LEDs or other specific light sources that produces a specific kind of dichroic light 34.

Both the magnetic pulsing 36 and the dichroic light 34 combined can treat depression, migraines and other psychiatric conditions by changing the direction of the magnetic current towards the targeted area of the brain in addition to the changing kind, color, and intensity, respectively, of the dichroic light 34 directed towards the eyes of the wearer. In certain embodiments, the eyewear 10 may provide a light sensor 14 electronically connected to the plurality of light sources 16 for facilitating the adjustability of their dichroic light's kind, color, and intensity. By manipulating the adjustable angle or light path, intensity, color and the type of dichroic light 34 along with changing the direction of the TMS magnetic pulsing 36, the eyewear 10 may treat certain head-related medical and mental health conditions. Each different combination of magnetic pulsing 36 and the dichroic light 34 has different applications for the different conditions.

In the present invention, magnetic pulse generator at the end of the stimulation arm 30 will generate transcranial magnetic stimulation on the desired spot of the brain. Stimulation of different areas of the brain will produce different effects. Prefrontal and parietal area for example can produce antidepressant effects. The continuous magnetic stimulation, even though it does not generate a great power, may produce the desired antidepressant effects by simple accumulation with extended time because of the extended period of daily time use of the eyewear 10. The plurality of light sources 16 will produce dichroic light 34 directed towards the interior side of nose bridge and will produce enough bright light with no glare to treat depression, for example. The combination of both technologies will maximize the effects of treatment.

A first and second switch 26 and 22 may be electrically connected to the electromagnetic generator system 28 for adjusting the type and intensity of the dichroic light 34 as well as the frequency and amplitude of the magnetic pulsing used for treatment. The eyewear 10 provides a microprocessor with a power source 24 coupled to the electromagnetic generator system 28, wherein the power source 24 may include rechargeable batteries and the like.

In the treatment, of migraine for example, the kind of light used, its color, and intensity is different than that used in treatment of depression. The user can wear the eyewear 10 all day, inside or outside of the house, if needed because of the transitional lenses technology of the optical lenses 12.

A method of using the present invention includes the following. The eyewear 10 disclosed above may be provided. A user may then develop a TMS and light therapeutic regime for their specific needs. The user then may don the eyewear 10 and choose one treatment option via manipulation of the first or second switch 26 and 22. For example, if the user chooses depression, then both technologies (dichroic light 34 and magnet pulsing 36) may be selectively operated and adjusted as described above. If the user chooses to treat a migraine, then magnetic pulsing 36 may work and the dichroic light 34 may switch to migraine light which is a special kind of light appropriate for migraines and not depression. If the person suffers from both depression and migraines, then the system will choose a special light that is OK for both depression and migraine while selectively operating the magnet pulsing system 28. When generating the magnetic pulsing 36 the user moves the stimulation arm up 30 to the operative condition so that the magnetic stimulation begins working on a specific area of the brain through the skull.

Additionally, the present invention can be used also to treat other conditions such as Schizophrenia, Bipolar, Anxiety disorder and Epilepsy. Also, the present invention can be incorporated into a baseball hat or headphone instead of sunglasses or eyeglasses.

It should be understood, of course, that the foregoing relates to exemplary embodiments of the invention and that modifications may be made without departing from the spirit and scope of the invention as set forth in the following claims.

What is claimed is:

1. A device, comprising:
a headwear adapted to be worn on a head of a human user;
an electromagnetic generator system provided by the headwear;
a stimulation arm electrically connected to the electromagnetic generator system and configured to emit magnetic pulsing created by the electromagnetic generator system, wherein the stimulation arm is pivotally connected to one of two frame arms of the headwear, the stimulation arm is configured to be moveable between a storage condition and an operative condition, wherein in the operative condition, the stimulation arm is configured to extend upwardly of said frame arm to position the stimulation arm adjacent a temple of the head of the human user; and
at least one switch disposed on the headwear that is coupled to the electromagnetic generator system, the at least one switch configured to select at least one of a frequency or an amplitude of the magnetic pulsing of the electromagnetic generator system.

2. A device, comprising:
an eyewear adapted to be worn on a face of a human user, the eyewear comprising:
 a frame defining two lens portions, wherein each lens portion engages a periphery of an optical lens; and
 two frame arms, each frame arm extending from a respective opposing end of the frame;
an electromagnetic generator system provided by the eyewear; and
a stimulation arm electrically connected to the electromagnetic generator system, wherein the stimulation arm is pivotally connected to one of the two frame arms, the stimulation arm is configured to extend upward form said frame arm to position the stimulation arm adjacent a temple of the human user while the device is worn by the human user.

3. The device of claim 2, further comprising:
a stimulation plate electrically connected to the electromagnetic generator system, wherein the stimulation plate is disposed between the two lens portions.

4. The device of claim 2, further comprising:
a plurality of light sources disposed along a lateral edge of at least one of the two lens portions, wherein the plurality of light sources provides dichroic light directed generally parallel to the respective optical lens.

5. The device of claim 2, wherein each optical lens is a transitional optical lens.

6. The device of claim 2, further compromising at least one switch electrically connected to the plurality of light sources and the electromagnetic generator system for selectively operating the dichroic light and a magnetic pulsing emitted therefrom, respectively.

7. A device, comprising:
an eyewear adapted to be worn on a face of a human user, the eyewear comprising:
a frame defining two lens portions, wherein each lens portion engages a periphery of an optical lens, wherein each optical lens is a transitional optical lens; and
two frame arms, each frame arm extending from a respective opposing end of the frame;
an electromagnetic generator system provided by the eyewear;
a stimulation arm electrically connected to the electromagnetic generator system, wherein the stimulation arm is pivotally connected to one of the two frame arms, the stimulation arm configured to be moveable between a storage condition and an operative condition, the stimulation arm is configured to extend upwardly of said frame arm to position the stimulation arm adjacent a temple of the human user while the device is worn by the human user;
a stimulation plate electrically connected to the electromagnetic generator system, wherein the stimulation plate is disposed between the two lens portions;
a plurality of light sources disposed along a lateral edge of at least one of the two lens portion, wherein the plurality of light sources provides dichroic light directed generally parallel to the respective optical lens; and
at least one switch electrically connected to the plurality of light sources and the electromagnetic generator system for selectively operating the dichroic light and a magnetic pulsing emitted therefrom, respectively.

* * * * *